(12) United States Patent
Wu et al.

(10) Patent No.: US 6,238,877 B1
(45) Date of Patent: May 29, 2001

(54) METHOD FOR PREDICTION PROSTATE CANCER PATIENTS' RESISTANCE TO HORMONAL TREATMENT BY MEASURING SERUM CONCENTRATIONS OF CHROMOGRANIN A

(75) Inventors: James T. Wu, Salt Lake City; Mark E. Astill, Centerville, both of UT (US)

(73) Assignee: ARUP Institute, Salt Lake City, UT (US)

( * ) Notice: Subject to any disclaimer, the term of this patent is extended or adjusted under 35 U.S.C. 154(b) by 0 days.

(21) Appl. No.: 09/187,095

(22) Filed: Nov. 5, 1998

Related U.S. Application Data (60) Provisional application No. 60/064,551, filed on Nov. 5, 1997.

(51) Int. Cl.[7] ........................ G01N 33/574; G01N 33/53; G01N 33/48; C12Q 1/68
(52) U.S. Cl. .............................. 435/7.23; 435/6; 435/7.1; 436/63; 436/64
(58) Field of Search ................................ 435/6, 7.1, 7.23; 436/63, 64

(56) References Cited

U.S. PATENT DOCUMENTS 4,758,522  7/1988  O'Connor ............................ 436/501

OTHER PUBLICATIONS

Papandreou et al., "Neutral endopeptidase 24.11 loss in metastatic human prostate cancer contributes to androgen–independent progression", Nature Medicine, (pp. 50–57), Jan. 1998, vol. 4, No. 1.

Pruneri et al., "Chromogranin A and B and Secretogranin II in Prostatic Andenocarcinomas: Neuroendocrine Expression in Patients Untreated and Treated with Androgen Deprivation Therapy", The Prostate, (pp. 113–120), 1998.

Wu et al., "Serum Chromogranin A: Early Detection of Hormonal Resistance in Prostate Cancer Patients", JCLA, (pp. 20–25), 1998

Koivisto et al., "Androgen Receptor Gene Amplification: A Possible Molecular Mechanism for Androgen Deprivation Therapy Failure in Prostate Cancer", Cancer Research, (pp. 314–319), Jan. 15, 1997.

Kimura et al., "Plasma Chromogranin A in Prostatic Carcinoma and Neuroendocrine Tumors", The Journal of Urology, (pp. 565–568), Feb. 1997.

Angelsen et al., "Neuroendocrine Differentiation in Carcinomas of the Prostate: Do Neuroendocrine Serum Markers Reflect Immunohistochemical Findings?", The Prostate, (pp. 1–6), 1997.

Angelsen et al., Use of Neuroendocrine Serum Markers in the Follow–up of Patients With Cancer of the Prostate, The Prostate, (pp. 110–117), 1997.

(List continued on next page.)

Primary Examiner—Anthony C. Caputa
Assistant Examiner—Jennifer Hunt
(74) Attorney, Agent, or Firm—Madson & Metcalf (57) ABSTRACT

The present invention relates to a method for early prediction of a prostate cancer patient's response to hormonal treatment. In one embodiment, the method of the present invention involves assaying a body fluid, such as plasma or serum, from a prostate cancer patient for the presence of elevated levels of chromogranin A (CgA). Elevated levels of CgA may indicate neuroendocrine differentiation of cells within the prostate tumor, and may require altering the patient's treatment. In a further embodiment of the method of the present invention, periodic assays for CgA are conducted for a patient undergoing hormonal treatment for prostate cancer. The results of these assays are correlated to determine if the patient's levels of CgA are high (greater than 100 ng/mL) or increasing. Such assays may also be carried out in conjunction with assays for total prostate specific antigen (tPSA).

2 Claims, 5 Drawing Sheets

OTHER PUBLICATIONS

Theodorescu et al., "Cathepsin D and Chromogranin A as Predictors of Long Term Disease Specific Survival after Radical Prostatectomy for Localized Carcinoma of the Prostate", CANCER, (pp. 2109–2119), 1997.

Wu et al., "Serum Chromogranin A: Early Detection of Hormonal Resistance in Prostate Cancer Patients", JCLA, (pp. 1–6), 1997.

Cussenot et al., "Plasma Neuroendocrine Markers in Patients With Benign Prostatic Hyperplasia and Prostatic Carcinoma", The Journal of Urology, (pp. 1340–1343), Apr. 1996.

di Sant'Agnese et al., "Neuroendocrine Differentiation in Prostatic Malignancy", CANCER, (pp. 357–361), Jul. 15, 1996.

Deftos et al., "Immumnoassay and Immunohistology Studies of Chromogranin A as a Neuroendocrine Marker in Patients with Carcinoma of the Prostate", Urology, (pp. 58–62), 1996.

di Sant'Agnese, "Neuroendocrine Differentiation in Prostatic Carcinoma", CANCER Supplement, (pp. 1850–1859), Apr. 1, 1995, vol. 75, No. 7.

Fowler et al., "Prostate Specific Antigen Regression and Progression After Androgen Deprivation for Localized and Metastatic Prostate Cancer", The Journal of Urology, (pp. 1860–1865), Jun. 1995.

Boomsma et al., "Sensitivity and specificity of a new ELISA method for determination of chromogranin A in the diagnosis of pheochromocytoma and nueroblastoma", Clinica Chimica Acta, (pp. 57–63), 1995.

Iacangelo et al., "Chromogranin A: current status as a precursor for bioactive peptides and granulogenic/sorting factor in the regulated secretory pathway", Regulatory Peptides, (pp. 65–88), 1995.

Kirchmair et al., "Large variations in the proteolytic formation of a chromogranin A–derived peptide (GE–25) in neuroendocrine tissues", Biochem, (pp. 331–336), 1995.

Öberg et al., "Measurements of chromogranin A, chromogranin B (secretogranin I), chromogranin C (secretogranin II) and pancreastatin in plasma and urine from patients with carcinoid tumours and endocrine pancreatic tumours", Journal of Endocrinology, (pp. 49–59), 1995.

di Sant'Agnese et al., "The Prostatic Endocrine–Paracrine (Neuroendocrine) Regulatory System and Neuroendocrine Differentiation in Prostatic Carcinoma: A Review and Future Directions in Basic Reasearch", The Journal of Urology, (pp. 1927–1931), Nov. 1994.

Flier et al., "Androgen Resistance—The Clinical and Molecular Spectrum", The New England Journal of Medicine, (pp. 611–618), Feb. 27, 1992.

Bender et al., "Immunoluminometric Assay of Chromogranin A in Serum with Commerically Available Reagents", Clinical Chemistry, (pp. 2267–2272), Nov. 11, 1992.

Kadmon et al., "Elevated Plasma Chromogranin–A Concentrations in Prostatic Carcinoma", The Journal of Urology, (pp. 358–361), Aug. 1991.

Tarle et al., "Investigation on Serum Neurone–Specific Enolase in Prostate Cancer Diagnosis and Monitoring: Comparative Study of a Multiple Tumor Marker Assay", NSE in Prostate Cancer, (pp. 22–33), 1991.

O'Connor et al., "Circulating Chromogranin A as a Diagnostic Tool in Clinical Chemistry", Acta histochemica, (pp. 27–33), 1990.

O'Connor et al., "Rapid Radioimmunoassay of Circulating Chromogranin A: In Vitro Stability, Exploration of the Neuroendocrine Character of Neoplasia and Assessment of the Effects of Organ Failure", Clinical Chemistry, (pp. 1631–1636), Nov. 8, 1989.

Dillen et al., "Enzyme–Linked Immunosorbent Assay for Chromogranin A", Clinical Chemistry, (pp. 1934–1938), Nov. 9, 1989.

Têtu et al., "Small Cell Carcinoma of the Prostate Part I", CANCER, (pp. 1803–1809), May 17, 1987.

Nordenstam et al., "Bacteriuria and Mortality in an Elderly Population", The New England Journal of Medicine, (pp. 1145–1152), May 1, 1986.

Landsberg, "Chromogranin A", The New England Journal of Medicine, (pp. 794–796), Sep. 20, 1984.

O'Connor, "Radioimmunoassay of Chromogranin A in Plasma as a Measure of Exocytotic Sympathoadrenal Activity in Normal Subjects and Patients with Pheochromocytoma", The New England Journal of Medicine, (pp. 764–770), Sep. 20 1984.

METHOD FOR PREDICTION PROSTATE CANCER PATIENTS' RESISTANCE TO HORMONAL TREATMENT BY MEASURING SERUM CONCENTRATIONS OF CHROMOGRANIN A

RELATED APPLICATIONS

This application is related to U.S. Provisional Application No. 60/064,551 of James T. Wu and Mark E. Astill filed Nov. 5, 1997 and entitled "Method for Predicting Prostate Cancer Patients' Resistance to Hormonal Treatment by Measuring Serum Concentrations of Chromogranin A," which provisional application is incorporated herein by reference.

FIELD OF THE INVENTION

The present invention relates to a method for early prediction of prostate cancer patients' response to hormonal treatment. More specifically, the present invention relates to measuring serum concentrations of chromogranin A to predict whether prostate cancer patients will respond favorably to hormonal treatment or whether alternative medical treatment should be sought.

TECHNICAL BACKGROUND

Neuroendocrine cells (or endocrine-paracrine cells, or amine precursor uptake and decarboxylation cells) are intraepithelial cells with hybrid neuroendocrine and epithelial characteristics. These cells are widely distributed within the urethroprostatic region, with cells in the prostatic and penile urethra, prostatic ducts, and peripheral prostate. Prostate neuroendocrine cells are regulatory cells. Often, prostate neuroendocrine cells contain a biogenic amine, usually serotonin. In addition, prostate neuroendocrine cells contain one or more neuropeptides. These neuropeptides include chromogranin A (CgA), neuron specific enolase (NSE), substance P, calcitonin, somatostatin, neurotensin, bombesin, and even parathyroid hormone-related protein and thyroid-stimulating hormone-like peptide with chain homology. Some subpopulations of neuroendocrine cells also contain epidermal growth factor receptor and c-erbB-2. This type of prostate cell co-proliferates as a malignant epithelial component in most, if not all, prostatic carcinomas—which has been overlooked until very recently.

Normal neuroendocrine cells of the prostate do not contain androgen receptor and, therefore, are not regulated by androgen. As a result, neuroendocrine differentiation usually is associated with the increase of the NSE and CgA markers and rises with the increase of hormonal resistance in prostate cancer. Apparently, neuroendocrine cells in the prostate tumor gain growth advantage during hormonal deprivation therapy; they not only proliferate after androgen ablation therapy, but also have a tendency of becoming malignant. Consequently, prostatic tumors with extensive neuroendocrine differentiation were found to behave aggressively and are usually associated with a poor prognosis. Nearly all, if not all, prostatic carcinomas have some degree of neuroendocrine differentiation.

Pure neuroendocrine malignancies of the prostate also can be found in small cell carcinoma and carcinoid-like tumors. The malignancies in both cases, while rare, are highly aggressive and malignant. Understandably, it is critical that neuroendocrine differentiation in prostatic tumor be detected early. Patients with prostate cancer ideally should be evaluated for new treatment strategies before tumors become malignant. Chemotherapeutic regimens similar to those used in small cell carcinoma of the lung have been found to be beneficial for small cell carcinoma of the prostate.

Two markers expressed by tumor tissues, CgA and NSE, have been used to detect neuroendocrine differentiation. Positive immunostain for both markers in the tumor tissue biopsies correlates with poor prognosis and short survival intervals. Whether their serum or plasma concentrations are useful—as prognostic markers, however, is unclear. Serum markers are a more global indicator and a more objective quantifier of the neuroendocrine differentiation of tumors. The serum concentration of CgA, for example, reflects the activity of not only the primary tumor, but also its associated metastasis. Researchers have found both elevated plasma CgA and NSE for prostate cancers showing hormonal resistance. They found that determining neuroendocrine differentiation by NSE or CgA immunoassays was not helpful in the prediction of progressive localized prostatic carcinoma. Other researchers have found elevated plasma CgA in 48% of 25 patients with stage D2 prostate cancer. In another study, researchers did not find any of their patients with carcinoma of the prostate who had elevated serum values of NSE, despite the presence of NSE-positive tumor cells in 77% of the tumors. However, they not only found elevated serum values of CgA in 59% of their patients, but also a positive correlation between the number of CgA-staining cells and the serum values of CgA. Accordingly, CgA is a more useful serum marker in predicting the extent of neuroendocrine differentiation in prostatic tumors.

Neuroendocrine cells are not only present in prostate tumor. In one study, small proliferating nodules of benign prostate hyperplasia (BPH) contained abundant serotonin positive neuroendocrine cells and 10.7% of patients with BPH had abnormally high NSE levels. In fact, many of the D2 prostate cancer patients containing low tPSA (less than 4 ng/mL) had elevated CgA in the serum. Therefore, CgA may complement the tPSA assay in order to diagnose the presence of cancer. Interestingly, researchers have observed that even though there were elevated serum CgA levels in BPH patients, the plasma CgA levels in BPH patients usually fell below 100 ng/mL, whereas 50% of their cancer patients (D2) had levels of CgA greater than 100 ng/mL. CgA is also the major soluble protein in catecholamine-storage vesicles, which is stored and released by exocytosis with catecholamines and has been a useful index of sympathoadrenal catecholamine release in laboratory animals.

Continued progression of prostate cancer during endocrine therapy is a major clinical problem. Many studies suggest that prostatic cell lines may be stimulated to invade with neuropeptides secreted by neuroendocrine cells. Certain neuroendocrine peptides can increase the invasive potential of prostatic carcinoma cells and may thereby contribute to the rapid progression and aggressive clinical course of prostate tumors containing neuroendocrine elements.

From the foregoing, it will be appreciated that it would be an advancement in the art to provide a method for detecting resistance during the hormonal treatment of prostate cancer to prevent further development of malignant tumors.

It would be a further advancement in the art if the method provided earlier detection of hormonal resistance in prostate cancer patients than currently available tPSA assays.

Finally, it would be another advancement in the art if the method differentiated between prostate cancer and BPH.

Such a method is disclosed and claimed herein.

BRIEF SUMMARY OF THE INVENTION

Chromogranin (CgA) and neuron specific enolase (NSE) in serial serum specimens from 14 patients with prostate cancer (CAP patients) showing resistance to hormonal treatment were monitored. Elevated serum CgA was detected in 10 out of these 14 patients (71%) during treatment, and an early appearance of elevated serum CgA was found in 6 of 14 (43%) of these patients when serum tPSA levels were still in the normal range. If patients with radical prostatectomy were not included, the percentage of patients showing an early appearance of elevated serum CgA would have been much higher. Elevated serum CgA levels also were found in patients not subject to hormonal therapy. Serial specimens from two out of three prostate cancer patients, randomly selected, contained elevated serum CgA. Serum NSE was not detectable in any of the serial specimens studied, suggesting that CgA, not NSE, is a marker for neuroendocrine differentiation. Also compared were the serum CgA in random serum specimens between patients with BPH (benign prostate hyperplasia) and with prostate cancer in which the concentration range of serum tPSA was between 3–15 ng/mL. Although serum CgA concentrations in BPH patients overlapped considerably with those levels in patients with prostate cancer, levels greater than 100 ng/mL should suggest prostate cancer. The early appearance of elevated serum CgA allow an early change of therapy to be made and can lead to the effective prevention of any further development of metastasis. More particularly, patients undergoing hormonal therapy can be monitored periodically for high (greater than 100 ng/mL) or increasing levels of CgA.

These and other objects and advantages of the present invention will become apparent upon reference to the accompanying drawings, graphs, detailed description and appended claims.

SUMMARY OF THE DRAWINGS

A more particular description of the invention briefly described above will be rendered by reference to the appended drawings and graphs. These drawings and graphs only provide information concerning typical embodiments of the invention and are not therefore to be considered limiting of its scope.

DETAILED DESCRIPTION OF THE INVENTION

Neuroendocrine differentiation, expression of bcl-2 oncoprotein (an apoptosis-suppressing oncoprotein), and an increase in the expression of a wild-type androgen receptor gene by prostate tumor can all lead to hormonal resistance in patients with prostate cancer. Therefore, it is peculiar to find elevated serum CgA in so many prostate cancer patients showing hormonal resistance. The importance of neuroendocrine differentiation in prostate cancer apparently had not been recognized in the past. It appears from this study that for many prostate cancer patients, the development of metastasis during the hormonal treatment is likely the result of neuroendocrine differentiation (detectable by measuring serum CgA). The ability of neuroendocrine cells in the prostate tumor to grow in an environment of depleted or low concentrations of serum androgen largely accounts for the failure of treatment for prostate cancer patients when subjected to hormonal treatment. The malignant behavior of neuroendocrine cells also explains why hormonal resistance is the major cause of death in patients with prostate cancer. Yet, it is encouraging to find in the method of the present invention that so many of these patients (43%) showed elevated serum CgA several months before the serum tPSA became elevated. Early appearance of serum CgA conceivably would create an opportunity for the early adjustment of therapy and the prevention of any further development of metastasis. In fact, among these 14 patients with hormonal resistance, the low serum CgA found in four patients could be due to the effect of earlier prostatectomy. In other words, the percentage of patients with early appearance of elevated serum CgA could be higher. The results of this study indicate that monitoring serum CgA should be carried out routinely and periodically during treatment, especially during hormonal therapy, in addition to the tPSA assay.

Figure 4:
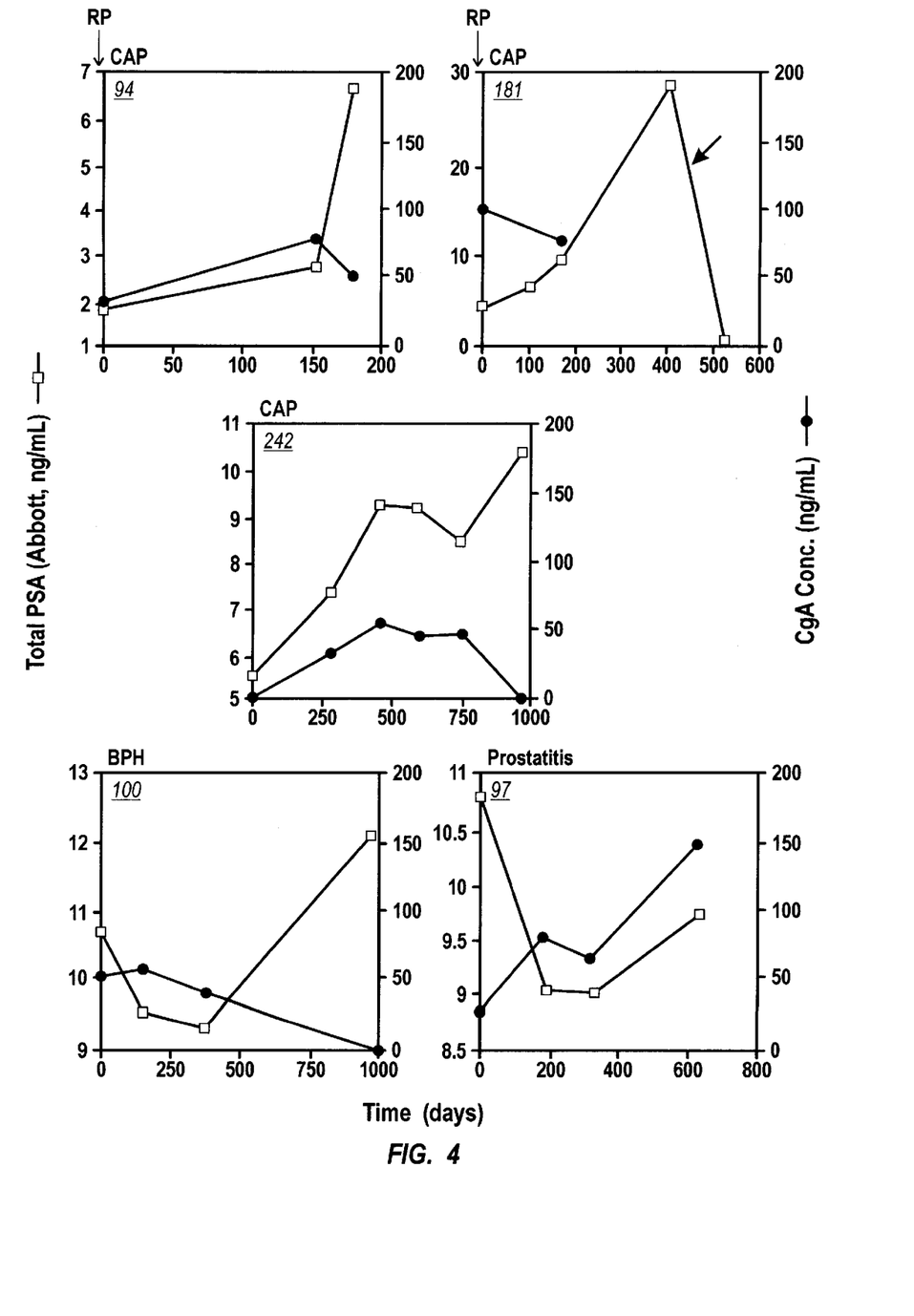
FIG. 4: Serum CgA in patients without hormonal treatment. Apparently the elevation of serum CgA also may account for the increase of tPSA levels and thus metastases for patients not subjected to hormonal treatment. Patients 94 and 181 showed an increase of tPSA following the earlier elevation of serum CgA; both had prostatectomy a few years earlier. The clinical situation presented in patient 242 is not clear. The significance of elevated serum CgA in patient 97 with prostatitis is also unknown. Arrow indicates orchiectomy was performed. CAP stands for carcinoma of the prostate, and RP refers to prostatectomy.

It appears that the importance of neuroendocrine differentiation is not limited to the development of hormonal resistance. Even among the few randomly selected serial specimens from prostate cancer patients not subjected to hormonal therapy, two out of three showed elevated serum CgA sometime during the disease course (FIG. 4). It has been suggested that prostatic neuroendocrine cells may promote prostate tumor proliferation by their secreted neuropeptides.

In the present invention, the frequent detection of elevated serum CgA in prostate cancer patients indicates the importance of monitoring serum CgA in all prostate cancer patients regardless of the treatment they were undergoing. It would be interesting to know how much the prostate cancer patients would benefit if treatment could be developed that lowered CgA serum concentrations.

CgA is the major soluble protein stored and released with catecholamines from vesicles in the adrenal medulla (chromaffin granules with chromaffin cell) and sympathetic nerve. It has a widespread neuroendocrine distribution, wherein it may be stored and released with various polypeptide hormones. The association of neuroendocrine differentiation and poor prognosis in prostate tumors reported in the literature were mostly based on studies examining the expression by the tumor tissue and immunostaining biopsies for chromogranin A. It was concluded that neuroendocrine differentiation is a significant predictor of poor survival. However, the relatively high levels of serum CgA detected in the BPH patients does not recommend the use of serum CgA to differentiate BPH from prostate cancer or as a prognostic marker during screening to predict risk of cancer. Yet when serum CgA is highly elevated, greater than 100 ng/mL, it is very likely that the person has cancer and not BPH.

Researchers have reported that both serum levels of NSE and CgA correlated with resistance to hormone ablation therapy and a poor prognosis in advanced prostate cancer. In the present invention, we failed to detect any significant serum NSE. Failure to detect elevated NSE indicates that immunostaining may sometimes detect only the storage of the marker and not active secretion. In this regard, serum levels may be a better marker that correlates with prognosis because only the secreted neuropeptides will exert physiological effects.

The normal reference levels are very different among various kits. Normal reference levels also would be useful for other diagnoses since the serum CgA also can be used as a marker for carcinoid tumors, pancreatic islet cell tumors, medullary carcinoma of the thyroid, and hyperparathyroidism and endocrine neoplasms, such as pheochromocytoma and neuroblastoma.

To better understand the details of the invention, the discussion of the invention below is divided into four parts: (1) Serum CgA in Prostate Cancer Patients Showing Hormonal Resistance; (2) Serum CgA Level in Nonhormonal Resistant Patients; (3) Comparison Between Serum CgA and NSE; and (4) Serum CgA in BPH and Prostate Cancer.

Serum CgA in Prostate Cancer Patients Showing Hormonal Resistance

Early Detection

Figure 1:
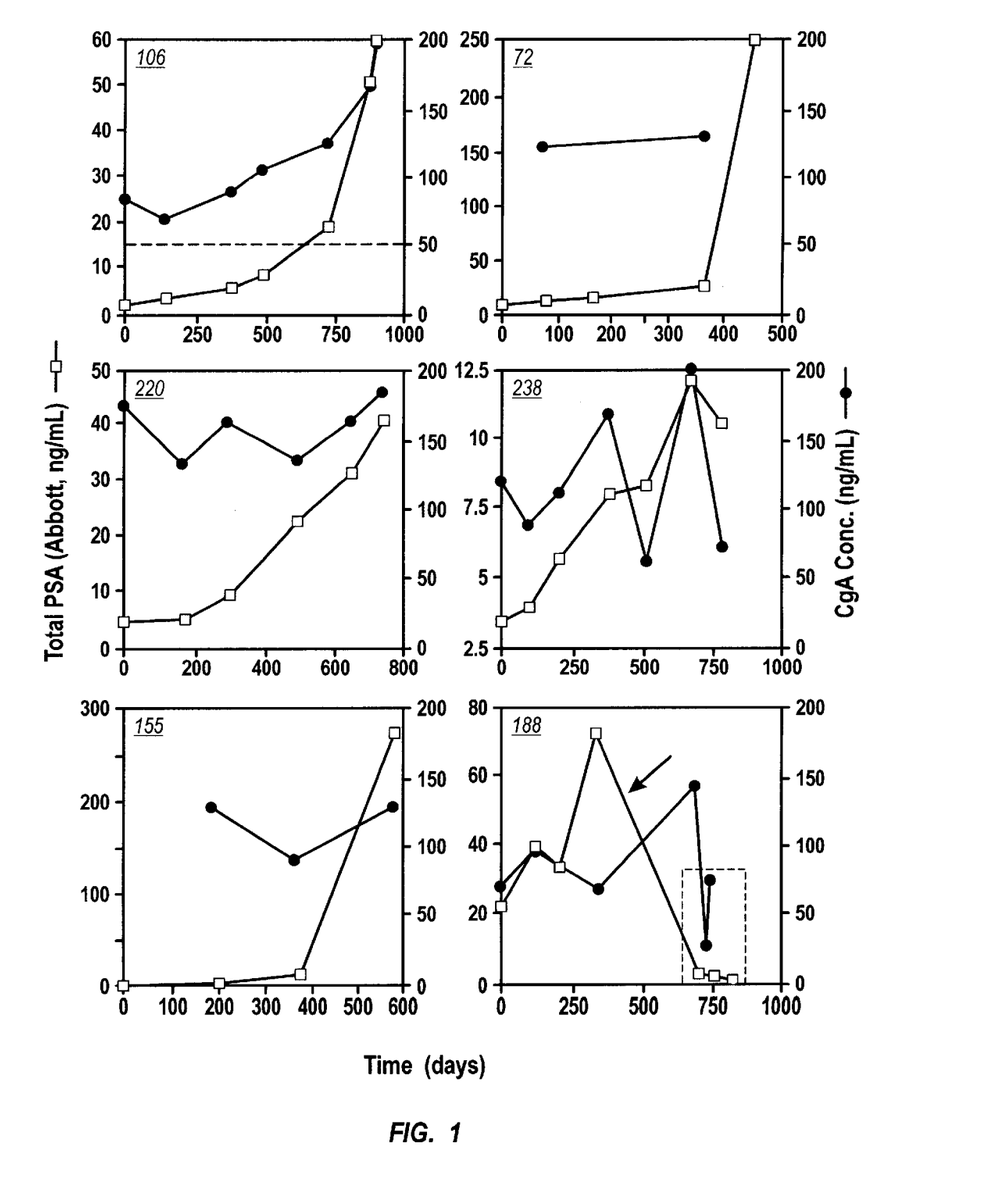
FIG. 1: Early appearance of elevated serum CgA in prostate cancer patients showing hormonal resistance. Hormonal resistance was demonstrated by the rise of serum tPSA after hormonal ablation following hormonal treatment. In all six patients, elevated serum CgA was detected when most serum tPSA were still less than 4 ng/mL. All patients except patient 188 had ablation performed a few years before the zero time shown in these figures. Patient 188 did not start hormonal treatment until after 500 days. The arrow in patient 188's plot indicates orchiectomy was performed at that time. The dotted square in patient 188 indicates elevated serum CgA despite low tPSA after orchiectomy.

In the present invention, serial serum specimens from 14 patients with prostate cancer showing hormonal resistance were used. All of the frozen specimens with known tPSA values (determined early with the Abbott assay on the IMx instrument) were retrieved from the freezer and subjected to CgA measurements. As illustrated in FIGS. 1–3, 10 out of 14 patients (71%) had elevated serum CgA concentrations. Importantly, in six of these 14 patients (43%), the serum CgA elevated much earlier than the elevation of serum tPSA. As shown in FIG. 1, in the majority of the cases, serum CgA levels were elevated while tPSA remained below 4 ng/mL (upper normal limit). Five patients shown in FIG. 1 had already received hormonal ablation. Patient 188 had hormonal ablation 500 days later as indicated. Patient 155 received both radiation therapy and hormonal treatment. The rest of these patients received hormonal treatment alone. According to the kit insert, the upper normal limit for CgA specimens is 54 ng/mL. Although this upper normal limit needs to be further verified (horizontal dotted line in FIG. 1), the value serves as an indication as to how highly elevated most of the CgA levels were. It was surprising to find such a large proportion of hormonal resistant patients showing elevated serum CgA, especially appearing at such an early stage when the tPSA level was still within the normal range. This early appearance of elevated CgA, if detected, would allow changes in treatment to be made sooner, increasing the probability of intervention before the tumor progresses to metastasis. For instance, for patient 72 the first tPSA value was only slightly elevated at 8.3 ng/mL. By contrast, the serum CgA concentration, which was greater than 100 ng/mL at this initial point and continually climbed, would have more accurately established the prognosis. The highly elevated serum CgA concentration in patient 72 would suggest the presence of neuroendocrine differentiation and the likely development of hormonal resistance. The slow rising of the tPSA concentrations over time at the early stages, by contrast, might not give the impression that the tumor was aggressive. Based on the tPSA values, one skilled in the art would have concluded that the tumor was still organ confined. In sum, the monitoring of serum CgA during hormonal treatment provides a means of early prediction. Monitoring serum CgA enables therapy to be adjusted in the crucial early stages leading to more effective measures which can be taken to prevent the development of malignant tumors.

Absence of Early Appearance of Serum CgA

Figure 2:
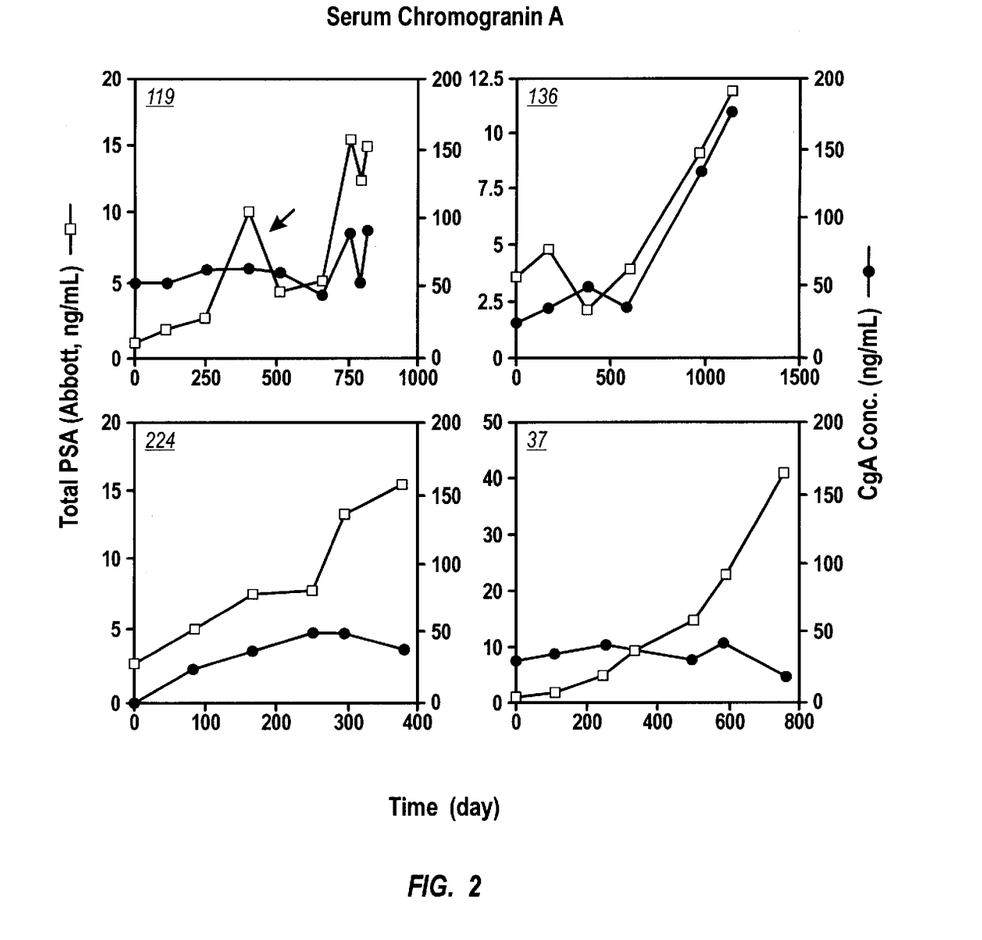
FIG. 2: Absence of early appearance of serum CgA in prostate cancer patients showing hormonal resistance. Serum CgA concentrations rose at later stages of the disease course and coincided with the increase of tPSA levels. Patients 224 and 37 did not show elevation of serum CgA at all. The arrow in patient 119's plot indicates orchiectomy was performed at that time.

In FIG. 2, the plots of four prostate cancer patients with hormonal resistance also show elevation of serum CgA at some point during the course of treatments, although the appearance of elevated serum CgA was no more heightened than the concentration of tPSA. None of them displayed the benefit of early detection as demonstrated in FIG. 1. However, if one undertakes a close, careful examination of the plots, especially of patients 119 and 136, one finds that the tPSA levels of these patients were not highly elevated, in contrast to the chromogranin A serum levels. These results consistently support the importance of monitoring serum CgA during hormonal treatment. Both patients 119 and 136 had received hormonal ablation earlier.

After Prostatectomy

Figure 3:
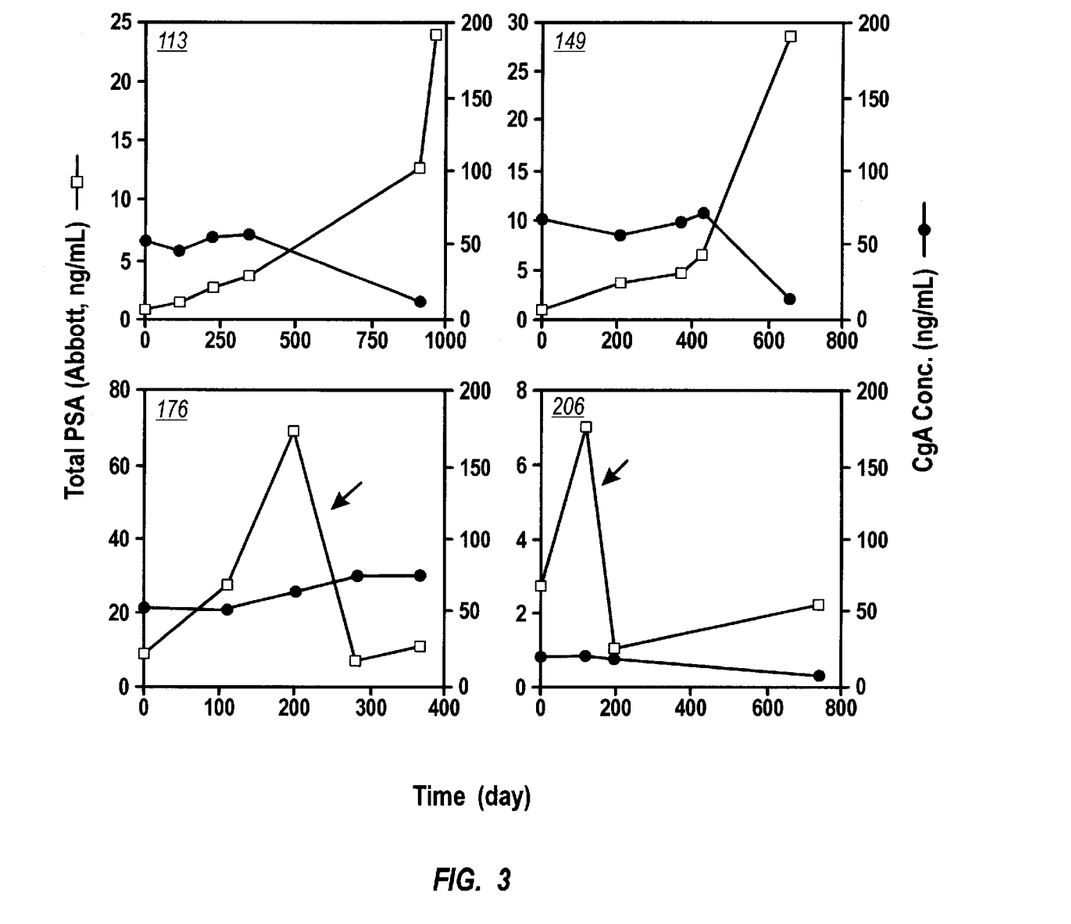
FIG. 3: Effect of prostatectomy on the serum levels of CgA in prostate cancer patients showing hormonal resistance. These patients did not have highly elevated serum CgA, as compared to cases shown in FIG. 1. Also, there was an absence of early appearance of elevated serum CgA. The presence of many fewer tumor cells to produce CgA after prostatectomy may account for the lack of highly elevated CgA. The arrow indicates orchiectomy was performed at that time.

All patients shown in FIG. 3 had received radical prostatectomy a few years earlier. The low and only moderately elevated serum CgA levels found in this group of prostate cancer patients could have been affected by the operation of radical prostatectomy. After prostatectomy it would be understandable if there were few tumor cells left to produce CgA. If tPSA were monitored during recurrence, one would not expect highly elevated serum CgA to accompany the appearance of tPSA. Therefore, there would not be any advantages to measuring both CgA and tPSA, nor much reason to hope for early detection with CgA while monitoring for recurrence. However, it would be beneficial to start measuring serum CgA as soon as treatment begins. As demonstrated with patient 176, the presence of elevated serum CgA following orchiectomy would indicate that patient was going to develop resistance to hormonal treatment. The much slower rise of tPSA confirmed that this was the case, but this would not have been clear until several months later.

Serum CgA Level in Nonhormonal Resistant Patients

The importance of neuroendocrine differentiation does not appear to be limited to prostate cancer with hormonal resistant. As illustrated in FIG. 4, elevated serum CgA was detected in specimens from patients with prostate cancer not undergoing hormonal treatment. Although orchiectomy was performed for patients NM and MJF (indicated by dramatic decrease of tPSA concentrations), elevated CgA were detected prior to that procedure. Elevated serum CgA was also detected in a patient with prostatitis (see FIG. 4, patient 97). Whether the elevation of CgA accounted for the elevation of tPSA in that patient is not known. Again, there is no explanation for the decrease of serum CgA observed in FIG. 4 patients. More studies will be needed to understand what causes the fluctuation of CgA in the serum in non-hormonal resistant patients. The rise and fall of serum CgA may provide additional information leading to the improved treatment of prostate cancer patients.

Comparison Between Serum CgA and NSE

Since NSE and CgA were both believed markers for neuroendocrine differentiation, both CgA and NSE in sera from prostate cancer patients showing hormonal resistance were measured. However, no elevation of NSE in the serum specimens was observed. Apparently NSE, which was frequently detected during neuroendocrine differentiation by immunohistochemical technique, was not released into the bloodstream. Therefore serum CgA, not serum NSE, should be monitored for detecting neuroendocrine differentiation in prostate cancer.

Serum CgA in BPH and Prostate Cancer

Figure 5:
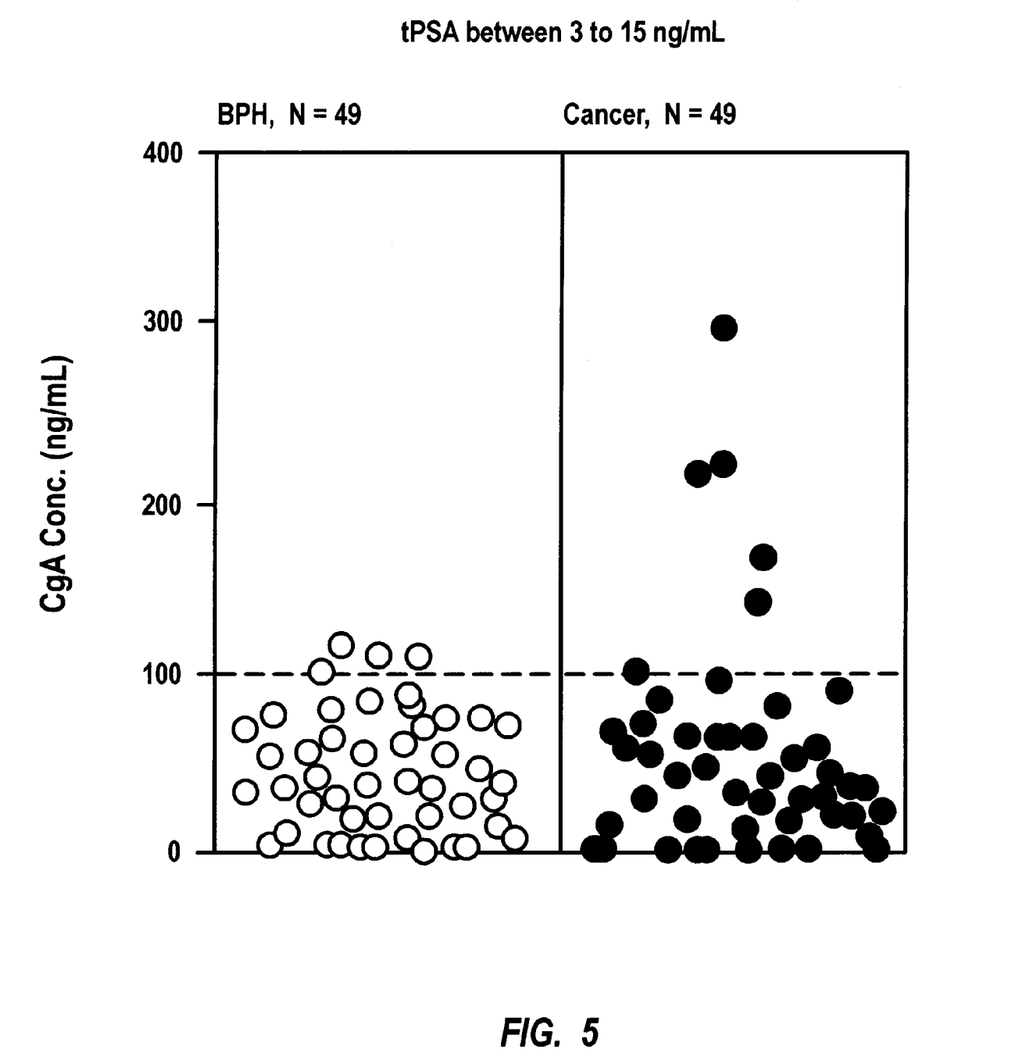
FIG. 5: Comparison of serum CgA concentrations of random specimens from patients with BPH and prostate cancer. Only specimens containing tPSA between 3–15 ng/mL were included in this study.

As illustrated in FIG. 5, CgA in random serum specimens from patients with either BPH or prostate cancer were measured to determine whether higher concentrations of serum CgA correlated with prostate cancer. It has been repeatedly demonstrated that when tissue sections of prostate tumor immunostain positive for CgA, poor prognosis was predicted. Therefore, it is reasonable to anticipate a finding of elevated serum CgA in prostate cancer patients. However, the relatively high serum CgA concentrations found in BPH specimens did not make serum CgA as effective as a prognostic marker as it proved for tumor tissue.

By measuring plasma CgA concentrations in patients with BPH, prostatitis and prostatic cancer, researchers have found that the plasma CgA concentration in patients with benign prostate diseases were all below 100 ng/mL, whereas 48% of D2 prostatic cancer patients contained plasma CgA above that level. In the present invention, a similar relationship between serum specimens from BPH and prostate cancer patients (FIG. 5) was observed, even though the specimens selected in FIG. 5 only contained tPSA in the concentration range between 3–15 ng/mL, whereas the specimens previously studied had much wider and higher concentrations of tPSA. It is reasonable to assume that more elevated and higher CgA concentrations would have been found in specimens containing highly elevated tPSA. Nevertheless, as shown in FIG. 5, the majority of the serum CgA concentration in patients with BPH, in general, were less than 100 ng/mL; only three specimens showed CgA slightly above 100 ng/mL. However, 12% of the prostate cancer patients had serum CgA concentration greater than 100 ng/mL. Apparently, the measurement of serum CgA concentration is not very useful for the differentiation of prostate cancer from BPH when tPSA levels are in the concentration range of 3–15 ng/mL. However, it is also likely that when the serum CgA concentration is greater than 100 ng/mL, the patient has prostate cancer.

EXAMPLES

The following examples are given to illustrate various embodiments which have been made with the present invention. It is to be understood that the following examples are not comprehensive or exhaustive of the many types of embodiments which can be prepared in accordance with the present invention.

Example 1

Immunoradiometric assay of Chromogranin A. CGA-RIACT, a solid-phase, two-site immunoradiometric assay for the measurement of human chromogranin A, was provided by CIS Bio International (Bagnols-sur-Ceze, France). According to the kit insert, if serum specimens are used, the upper normal limit is 54 ng/mL (mean+1 SD). The serum PSA (or tPSA) was performed on Abbott IMx using Abbot kit.

Example 2

Immunoradiometric Assay of Serum NSE. Serum NSE (neuron specific enolase) concentrations were determined using the ELSA-NSE kit, from CIS Bio International. This is a solid phase, two-site immunoradiometric assay using two monoclonal antibodies prepared against sterically remote antigenic sites on the NSE molecule.

Example 3

Serum Specimens. All serum specimens were obtained from the Department of Urology, University of Utah School of Medicine. Diagnoses associated with the majority of the samples, whether from patients with BPH or with prostate cancer, were confirmed by clinical biopsies. All specimens had Abbott PSA measured immediately after blood drawn and were then kept frozen at −70° C. for different lengths of time, several months to several years, before they were subjected to other measurements.

REFERENCES

The following references are incorporated by reference to the extent that they supplement, explain, or provide background for, or teach methodology, techniques or compositions employed herein:

1. di Sant' Agnese P A, Cockett A T K: Neuroendocrine differentiation in prostatic malignancy. Cancer 78:357–361, 1996.
2. Tetu B, Ro J Y, Ayala A F, Johnson D E, Logothetis C J, Ordonez N G: Small cell carcinoma of the prostate: Part 1. A clinicopathologic study of 20 cases. Cancer 59:1803, 1987.
3. di Sant' Agnese P A, Cockett A T I C—The prostatic endocrine-paracrine (Neuroendocrine) regulatory system and neuroendocrine differentiation in prostatic carcinoma: A review and future directions in basic research. J Urol 152:1927–1937, 1994.
4. di Sant' Agnese P A: Neuroendocrine differentiation in prostatic carcinoma. Recent findings and new concepts. Cancer 75:1850–1859, 1995.
5. Cussenot O, Vdlette J M, Valeri A, Cariou G, Descrandschamps F, Cortesse A, Meria P, TeUlac P, Fiet J, Le Duc A: Plasma neuroendocrine markers in patients with benign prostatic hyperplasia and prostatic carcinoma. J Urol 155:1340–1343, 1996.
6. Kadmon D, Thompson T C, Lynch G R, Scardino P T. Elevated plasma chromogranin A concentrations in prostatic carcinomas. J Urol 146:358–361, 1991.
7. Angelsen A, Syversen U, Haugen O A, Stridsberg M, Kjolnerod O K, Waldum H L: Neuroendocrine differentiation in carcinomas of the prostate: Do neuroendocrine serum markers reflect immunohistochemical findings? Prostate 30:16, 1997.
8. Cockett A T K, Di Sant'Agnese P A, Gopinath P, Schoen S. Abrahamsson P A: Relationship on neuroendocrine cells of prostate and serotonin to benign prostatic hyperplasia. Urology 42:512, 1993.
9. Hoosein, Logothetis, Chung: Differential effects of peptide hormones bombesin, vasoactive intestinal polypeptide and somatostatin analog RC-160 on the invasive capacity of human prostatic carcinoma cells. *J Urol* 149:1209–1213, 1993.
10. Raffo A J, Perlman H, Chen M-W, Day M L, Streitinan J S, Buttyan R: Overexpression of bcl-2 protects prostate cancer cells from apoptosis in vitro and confers resistance to androgen depletion in vivo. *Cancer Res* 55:4438–4445, 1995.
11. Koivisto P, Kononen J, Palmberg C, Tanu-nela T, Hyytinen E, Isola 1, Trapman J. Cleutjens K, Noordzij A, Voisakorpi T. Kallioniemi O-P: Androgen receptor gene amplification: A possible molecular mechanism for androgen deprivation therapy failure in prostate cancer. *Cancer Res* 57:314–319, 1997.
12. Tarle M, Rados N: Investigation on serum neuron-specific enolase in prostate cancer diagnosis and monitoring: comparative study of a multiple tumor marker assay. *Prostate* 19:23–27, 1991.

We claim:

1. A method for detection of resistance to hormonal therapy in a patient having prostate cancer prior to the development in said patient of elevated levels of prostate specific antigen (PSA), said method comprising the steps of performing periodic assays of serum samples from said patient to determine said patient's serum levels of chromogranin A and analyzing said samples for an increase in the serum levels of chromogranin A to greater than 54 ng/ml, wherein an increase in the patient's serum levels of chromogranin A to greater than 54 ng/ml is indicative of resistance to hormonal therapy.

2. The method of claim 1, wherein said samples are analyzed for an increase in the serum levels of chromogranin A to greater than 100 ng/mL.

* * * * *